(12) United States Patent
Li et al.

(10) Patent No.: US 9,078,997 B2
(45) Date of Patent: Jul. 14, 2015

(54) CATHETER ASSEMBLY INCLUDING COILED INTERNAL BOLSTER

(75) Inventors: Changqing Li, Ellettsville, IN (US);
Ken Brown, West Lafayette, IN (US);
Alan Sundheimer, Ellettsville, IN (US);
Boyd Colvin, Indianapolis, IN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 756 days.

(21) Appl. No.: 12/079,954

(22) Filed: Mar. 29, 2008

(65) Prior Publication Data

US 2009/0024091 A1      Jan. 22, 2009

Related U.S. Application Data

(60) Provisional application No. 60/920,601, filed on Mar. 29, 2007.

(51) Int. Cl.
*A61M 25/04* (2006.01)
*A61M 25/00* (2006.01)
(Continued)

(52) U.S. Cl.
CPC ............ *A61M 25/04* (2013.01); *A61J 15/0023* (2013.01); *A61J 15/0038* (2013.01); *A61B 17/3415* (2013.01); *A61M 1/285* (2013.01); *A61M 3/02* (2013.01); *A61M 3/0225* (2013.01);
(Continued)

(58) Field of Classification Search
CPC ............ A61M 25/0041; A61M 1/285; A61M 2025/0063; A61M 25/0015; A61M 25/0017; A61M 27/008; A61M 3/02; A61M 3/0225; A61M 24/04; A61J 15/0038; A61J 15/0023
USPC .......... 604/104, 105, 174, 175, 910, 106–109
See application file for complete search history.

(56) References Cited

U.S. PATENT DOCUMENTS 3,397,699 A      8/1968   Kohl
3,865,666 A  *  2/1975   Shoney ........................ 156/245

(Continued)

FOREIGN PATENT DOCUMENTS

WO      WO 00/23136 A1      4/2000
WO      WO 00/48656 A1      8/2000
WO      WO 2007/035526 A2   3/2007

*Primary Examiner* — Kevin C Sirmons
*Assistant Examiner* — Lauren M Peng
(74) *Attorney, Agent, or Firm* — Fay Kaplun & Marcin, LLP (57) ABSTRACT

A catheter assembly including a medical catheter and an internal bolster. In a preferred embodiment, the catheter is an elongated, tubular structure preferably made of a flexible, biocompatible material. The catheter is shaped to include a generally cylindrical wall terminating in a first end and in a second end, the wall coaxially surrounding and defining a longitudinal bore preferably used to convey fluids, such as food and/or medications, to a patient in need thereof. The internal bolster is an elongated, semi-tubular structure preferably made of a flexible, biocompatible material. The bolster is resiliently and reversibly transformable between a generally planar shape, when at rest, and a straightened shape, when forcibly unfurled. The bolster has an inner end and an outer end, the inner end being generally centrally located. The inner end of the bolster is insert-molded around the first end of the catheter, with the catheter and the bolster being oriented relative to one another so that the longitudinal axis of the catheter extends generally perpendicularly to the plane of the bolster in its coiled state, with the open, semi-tubular structure of the bolster facing away from the catheter.

21 Claims, 11 Drawing Sheets

(51) Int. Cl.
  *A61M 27/00* (2006.01)
  *A61M 1/28* (2006.01)
  *A61M 3/02* (2006.01)
  *A61J 15/00* (2006.01)
  *A61B 17/34* (2006.01)

(52) U.S. Cl.
  CPC ........ *A61M 25/0015* (2013.01); *A61M 25/0017* (2013.01); *A61M 25/0041* (2013.01); *A61M 27/008* (2013.01); *A61M 2025/0063* (2013.01)

(56) References Cited

U.S. PATENT DOCUMENTS

| | | | |
|---|---|---|---|
| 4,393,873 A | 7/1983 | Nawash et al. | |
| 4,488,877 A * | 12/1984 | Klein et al. | 604/175 |
| 4,834,725 A | 5/1989 | Iwatschenko | |
| 4,861,334 A | 8/1989 | Nawaz | |
| 4,863,438 A | 9/1989 | Gauderer et al. | |
| 4,900,306 A | 2/1990 | Quinn et al. | |
| 4,944,732 A | 7/1990 | Russo | |
| 5,007,900 A | 4/1991 | Picha et al. | |
| 5,071,405 A | 12/1991 | Piontek et al. | |
| 5,080,650 A * | 1/1992 | Hirsch et al. | 604/104 |
| 5,112,310 A * | 5/1992 | Grobe | 604/175 |
| 5,167,627 A | 12/1992 | Clegg et al. | |
| 5,279,564 A * | 1/1994 | Taylor | 604/104 |
| 5,308,325 A | 5/1994 | Quinn et al. | |
| 5,356,391 A | 10/1994 | Stewart | |
| 5,358,488 A | 10/1994 | Suriyapa | |
| 5,391,159 A | 2/1995 | Hirsch et al. | |
| 5,484,420 A * | 1/1996 | Russo | 604/178 |
| 5,720,734 A | 2/1998 | Copenhaver et al. | |
| 5,836,924 A | 11/1998 | Kelliher et al. | |
| 6,030,364 A | 2/2000 | Durgin et al. | |
| 6,223,070 B1 * | 4/2001 | Chait | 600/433 |
| 6,364,858 B1 | 4/2002 | Picha | |
| 6,402,722 B1 | 6/2002 | Snow et al. | |
| 6,743,198 B1 * | 6/2004 | Tihon | 604/104 |
| 6,852,105 B2 * | 2/2005 | Bolmsjo et al. | 604/544 |
| 7,087,041 B2 * | 8/2006 | von Dyck et al. | 604/332 |
| 7,201,738 B1 * | 4/2007 | Bengmark | 604/170.03 |
| 2003/0109830 A1 | 6/2003 | Picha et al. | |
| 2004/0059293 A1 | 3/2004 | Chu et al. | |
| 2006/0052752 A1 * | 3/2006 | McMichael | 604/175 |

\* cited by examiner

Coil 1
Coil 2

FIG. 7

3D Sphere

FIG. 8

3D Cone

FIG. 9

CATHETER ASSEMBLY INCLUDING COILED INTERNAL BOLSTER

CROSS-REFERENCE TO RELATED APPLICATIONS

The present application claims the benefit under 35 U.S.C. 119(e) of U.S. Provisional Patent Application Ser. No. 60/920,601, filed Mar. 29, 2007, the disclosure of which is incorporated herein by reference.

BACKGROUND OF THE INVENTION

The present invention relates generally to medical catheters and relates more particularly to medical catheters of the type having an internal bolster disposed at one end of said medical catheter for retaining said end of said medical catheter within a patient.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. (A less common approach involves jejunostomy, i.e., the creating of a feeding tract or stoma leading into the patient's jejunum.) Feeding is then typically performed by administering food through a catheter or feeding tube that has been inserted into the feeding tract, with one end of the feeding tube extending into the stomach and being retained therein by an internal anchor or bolster and the other end of the feeding tube extending through the abdominal wall and terminating outside of the patient.

Although gastrostomies were first performed surgically, most gastrostomies are now performed using percutaneous endoscopy and result in the implantation in the patient of a feeding tube/internal bolster assembly (said feeding tube/internal bolster assembly also commonly referred to as a percutaneous endoscopic gastrostomy (PEG) device). Two of the more common percutaneous endoscopic techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

According to the push method, one end of an endoscope is intubated (i.e., inserted) into a patient's mouth and is passed through the esophagus into the stomach. After distension of the stomach by inflation, an entry site on the abdomen is identified using the endoscope for transillumination, and an incision is made by passing the tip of a needle coupled to an outer cannula through the abdominal and stomach walls and into the stomach. One end of the outer cannula remains outside of the body and acts as a stop to limit insertion of the needle and outer cannula into the stomach. A snare is inserted into the stomach via the endoscope and is looped over the inserted end of the needle. The snare is then "walked" up the needle until the outer cannula is snared. The snared cannula is then pulled externally to tack the cannula to the stomach and, in turn, to secure the stomach wall to the abdominal wall. The needle is then removed from the patient while keeping the cannula in place. A first end of a flexible guidewire (also known in the art as a "pushwire") is then passed through the cannula and into the stomach where it is grasped by the snare, the second end of the guidewire remaining external to the patient. The endoscope and the snare are then withdrawn from the mouth of the patient to deliver the first end of the guidewire.

A push-type catheter implanting assembly is then inserted over the first end of the guidewire and is pushed over the guidewire towards its second end. The push-type catheter implanting assembly typically comprises a gastrostomy feeding tube, the gastrostomy feeding tube having a dome-shaped internal bolster disposed at its trailing end and having a tubular dilator serially connected to its leading end. The gastrostomy feeding tube and the internal bolster are typically made of a soft, biocompatible material, like silicone rubber, and typically form a unitary structure. The dilator, which tapers in outer diameter from its trailing end to its leading end, is typically made of polyethylene or a like material which is stiffer than silicone but which still possesses some flexibility. Advancement of the push-type catheter implanting assembly over the guidewire continues until the front end of the dilator reaches the cannula and pushes the cannula out through the abdominal wall of the patient. The front end of the dilator is then pulled through the abdominal wall until the front end of the gastrostomy feeding tube emerges from the abdomen and, thereafter, the internal bolster at the rear end of the gastrostomy feeding tube engages the stomach wall. The guidewire is then removed from the patient. The clinician then re-intubates the patient with the endoscope and uses an optical channel in the endoscope to inspect whether the internal bolster is properly seated in the stomach.

If the internal bolster is properly placed against the stomach wall, a length of the externally-extending portion of the implanted gastrostomy feeding tube is then typically cut and removed from the implanted tube to reduce the externally-extending portion of the tube to a desired length (typically about 4-6 inches). (The removal of the leading end of the gastrostomy feeding tube also results in the removal of the dilator, which is connected thereto.) An external bolster is typically secured to the remaining externally-extending portion of the feeding tube to engage the abdomen in such a way as to prevent longitudinal movement of the feeding tube into the stomach. Additionally, a "Y-port" adapter is typically attached to the external end of the feeding tube, the Y-port adapter being adapted to receive a pair of connector tips through which food and/or medications may be dispensed. In addition, a detachable locking clip is typically secured to the implanted feeding tube at a point between the external bolster and the Y-port adapter to prevent gastric fluids from escaping through the proximal end of the feeding tube when the feeding tube is not in use.

The pull method is similar in some respects to the above-described push method, the pull method differing from the push method in that, after the cannula is snared and the needle is removed therefrom, a looped first end of a suture (also known in the art as a "pullwire") is inserted through the cannula and into the stomach where it is grasped by the snare, the second end of the suture remaining external to the patient. The endoscope and the snare are then withdrawn from the mouth of the patient to deliver the first end of the suture. The first end of the suture is then coupled to the leading end of a pull-type catheter implanting assembly, the pull-type catheter implanting assembly typically comprising a gastrostomy feeding tube having an internal bolster integrally formed at its trailing end and a plastic fitting attached to its leading end. The plastic fitting typically has a barbed rear portion mounted within the leading end of the feeding tube and a conical front portion that serves as a dilator, said conical front portion tapering in diameter from the leading end of the feeding tube to a front tip. A wire loop is fixed to the front tip of the plastic fitting, the first end of the suture being tied to the wire loop. Using the second end of the suture, the pull-type catheter implanting assembly is then pulled retrograde through the patient until the gastrostomy feeding tube emerges from the abdomen of the patient and the internal bolster engages the stomach wall of the patient. Next, as is the case in the push method, the clinician then re-intubates the patient with the endoscope in order to visually inspect the placement of the internal bolster within the stomach. If the bolster is properly seated in the stomach, the externally-extending portion of the implanted gastrostomy feeding tube is then typically cut to a desired length and one or more of an external bolster, a Y-port and a clamp are attached to the feeding tube.

In addition to the above-described endoscopic techniques for implanting PEG devices, there also exist direct percutaneous techniques.

Typically, such direct percutaneous techniques involve (i) inserting an endoscope into the patient and, through transillumination, identifying a desired insertion site; (ii) using sutures or T-fasteners, placed one at a time, to secure the abdominal wall to the stomach wall in a plurality of locations surrounding the future insertion site; (iii) using a scalpel to make an incision at the insertion site; (iv) using a series of dilators to enlarge the insertion site opening until said opening is large enough to pass therethrough the internal bolster at the distal end of a gastrostomy tube; and (v) sliding an external bolster over the proximal end of the gastrostomy tube down to skin level over the T-fastener wires or sutures.

Another type of direct percutaneous technique is disclosed in U.S. Pat. No. 6,030,364, inventors Durgin et al., which issued Feb. 29, 2000, and which is incorporated herein by reference. In this patent, there is disclosed a method and apparatus for the percutaneous placement of gastro-intestinal tubes, the apparatus comprising a longitudinal penetration device; a hollow, tapered dilator; and a sheath having a central lumen extending therethrough. The penetration device is placed within the sheath, pushed distally to penetrate the target organ, and then removed from the sheath. After the penetration device is removed, the dilator is inserted into the central lumen of the sheath until it penetrates the target organ, so that the sheath and the penetration are radially dilated as the dilator passes through the sheath. The sheath is then pulled in the proximal direction to counter-balance the distal insertion force. A gastro-intestinal tube is inserted into the hollow center, and pushed distally until it exits the distal end of the dilator. The dilator and sheath are then removed from the target organ.

Still another type of direct percutaneous technique is disclosed in U.S. Pat. No. 6,402,722, inventors Snow et al., which issued Jun. 11, 2002, and which is incorporated herein by reference. In this patent, there is disclosed an apparatus and method for percutaneously placing gastrostomy tubes. The method enables percutaneous placement through an existing penetration, as well as placement where no penetration exists. The apparatus comprises a gastrostomy tube having an internal bolster which can be manipulated such that it has a reduced lateral extent; an axially-extending hollow sleeve which can surround the bolster to hold it in a position of reduced lateral extent; and a rip-cord capable of tearing the sheath. In a preferred embodiment, the internal bolster is folded to have a smaller diameter, the sleeve is placed over the bolster and shrunk down to a smaller diameter. The rip-cord runs distally along the outside of the tube, between the sleeve and the internal bolster, wraps over the distal end of the sleeve and runs proximally along the length of the tube. The replacement tube can then be pushed through a stoma. Once in place, the rip cord is pulled to tear away the sleeve, thereby allowing the bolster to revert to its original lateral extent.

Still yet another type of direct percutaneous technique is disclosed in U.S. Published Patent Application No. US-2004-0059293-A1, which was published Mar. 25, 2004, and which is incorporated herein by reference.

Other patents of interest include U.S. Pat. No. 5,936,924, inventors Kelliher et al., issued Nov. 17, 1998; U.S. Pat. No. 5,720,734, inventors Copenhaver et al., issued Feb. 24, 1998; U.S. Pat. No. 5,358,488, inventors Surlyapa, issued Oct. 25, 1994; U.S. Pat. No. 5,071,405, inventors Piontek et al., issued Dec. 10, 1991; U.S. Pat. No. 5,007,900, inventors Picha et al., issued Apr. 16, 1991; U.S. Pat. No. 4,944,732, inventor Russo, issued Jul. 31, 1990; U.S. Pat. No. 4,863,438, inventors Gauderer et al., issued Sep. 5, 1989; and U.S. Pat. No. 4,393,873, inventors Nawash et al., issued Jul. 19, 1983; all of which are incorporated herein by reference.

SUMMARY OF THE INVENTION

It is an object of the present invention to provide a novel catheter assembly.

Therefore, according to one aspect of the present invention, there is provided a catheter assembly comprising a catheter assembly comprising (a) a catheter, said catheter having a first end and a second end; and (b) an internal bolster disposed at said first end of said catheter, said internal bolster, in a first state, having a generally planar shape; (c) wherein said catheter is generally perpendicular to said internal bolster in said first state.

According to one embodiment, the catheter is an elongated, tubular structure preferably made of a flexible, biocompatible material, such as a silicone rubber. The catheter is shaped to include a generally cylindrical wall terminating in a first end and in a second end, the wall coaxially surrounding and defining a longitudinal bore preferably used to convey fluids, such as food and/or medications, to a patient in need thereof. The internal bolster is an elongated, semi-tubular structure preferably made of a flexible, biocompatible material, such as a silicone rubber. The bolster is resiliently and reversibly transformable between a generally planar, coiled (i.e., spiral) shape, when at rest, and a straightened shape, when forcibly unfurled. The bolster has an inner end and an outer end, the inner end being generally centrally located. The inner end of the bolster is insert-molded around the first end of the catheter, with the catheter and the bolster being oriented relative to one another so that the longitudinal axis of the catheter extends generally perpendicularly to the plane of the bolster in its coiled state, with the open, semi-tubular structure of the bolster facing away from the catheter.

According to another embodiment, the internal bolster further includes an embedded wire having shape-memory properties.

According to another aspect of the invention, there is provided a catheter assembly comprising (a) a catheter, said catheter having a first end and a second end; and (b) an internal bolster disposed at said first end of said catheter, said internal bolster being semi-tubular.

According to still another aspect of the invention, there is provided a catheter assembly comprising (a) a catheter, said catheter having a first end, a second end and a longitudinal axis; and (b) an internal bolster, said internal bolster having a first end and a second end, said first end of said internal bolster being mounted on said second end of said catheter, said internal bolster, in a first state, being generally perpendicular to said longitudinal axis of said catheter.

According to still yet another aspect of the invention, there is provided a catheter assembly comprising (a) a catheter, said catheter having a first end, a second end, an outer diameter and a longitudinal axis; and (b) an internal bolster disposed at said first end of said catheter, said internal bolster being an elongated member having a first end, a second end and an outer diameter, said outer diameter of said elongated member substantially matching said outer diameter of said catheter, said internal bolster, in a first state, being generally perpendicular to said catheter.

According to a further aspect of the invention, there is provided a kit for use in implanting a catheter assembly in a patient, said kit comprising (a) a catheter assembly, said catheter assembly comprising (i) a catheter, said catheter having a first end and a second end, and (ii) an internal bolster disposed at said first end of said catheter, said internal bolster, in a first state, having a generally planar shape; (iii) wherein said catheter is generally perpendicular to said internal bolster in said first state; and (b) a delivery device, said delivery device being a tubular member appropriately dimensioned to be inserted over said catheter assembly from said second end of said catheter and to unfurl said resilient members.

For purposes of the present specification and claims, various relational terms like "top," "bottom," "proximal" and "distal" are used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration certain embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Referring now to FIGS. 1(a) through 1(e), there are shown perspective, side, top, bottom, and longitudinal section views, respectively, of a first embodiment of a catheter assembly constructed according to the teachings of the present invention, said catheter assembly being represented generally by reference numeral 11.

Catheter assembly 11 may include a medical catheter 13 and an internal bolster 15.

Catheter 13 may be an elongated, tubular structure, which may be made of a flexible, biocompatible material, such as silicone rubber. Catheter 13 may be shaped to include a generally cylindrical wall 17 terminating in a first end 19 and in a second end 21, wall 17 coaxially surrounding and defining a longitudinal bore 23. As will be discussed further below, longitudinal bore 23 may be used to convey fluids, such as food and/or medications, to a patient in need thereof. A series of ruler markings (not shown) may be printed on catheter 13 and may extend several inches from first end 19 in the direction of second end 21 to facilitate the cutting of catheter 13 to a desired length after catheter 13 has been implanted in a patient.

Internal bolster 15 may be an elongated, semi-tubular structure, which may be made of a flexible, biocompatible material, such as silicone rubber. Bolster 15 may be resiliently and reversibly transformable between a generally planar shape, when at rest, and a straightened shape, when unfurled. More specifically, when at rest, bolster 15 may have a coiled or spiral shape that lies in a plane generally perpendicular to the longitudinal axis of catheter 13; by contrast, when unfurled, bolster 15 may lie along the same axis as catheter 13. Bolster 15 may have an inner end 25 and an outer end 27, inner end 25 of bolster 15 being generally centrally located. As can be seen, first end 19 of catheter 13 and inner end 25 of bolster 15 may be joined together, and catheter 13 and bolster 15 may be oriented relative to one another so that, when at rest, the open, semi-tubular structure of bolster 15 faces away from catheter 13.

It should be understood that, although, in the present embodiment, bolster 15 is wound into approximately 1½ coils, bolster 15 is not limited to such a shape and may include a greater or lesser number of coils.

Although catheter assembly 11 may be constructed as a unitary structure, catheter assembly 11 may be made by forming catheter 13 by extrusion and then by insert-molding bolster 15 around first end 19 of catheter 13. More specifically, catheter 13 may be provided with a wall 17 that tapers in thickness as it approaches end 19, with inner end 25 of bolster 15 being molded over said tapered wall so that the outer diameter of catheter assembly 11 remains constant as one transitions from catheter 13 to bolster 15. However, it should be understood that, if such a uniformity in outer diameter is not needed, one could modify catheter 13 so that it its wall 17 has a uniform thickness throughout its length, with bolster 15 being insert-molded around end 19 of catheter 13. Catheter 13 may be made from a relatively low durometer silicone rubber, (e.g., approximately 20-50) and bolster 15 may be made from a relatively high durometer silicone rubber (e.g., approximately 70-80). In this manner, catheter 13 may be provided with a comparatively high degree of flexibility whereas bolster 15 may be provided with a comparatively high degree of rigidity to assist in its retention within a patient.

Referring now to FIGS. 2(a) through 2(e), there is schematically shown a first manner in which catheter assembly 11 may be implanted in a patient. (For illustrative purposes, catheter assembly 11 is herein shown as an initial placement PEG device being implanted in the stomach of a patient; however, it is to be understood that catheter assembly 11 may be either an initial placement device or a replacement device and may be implanted in the stomach of a patient or at other locations within a patient where the delivery and/or drainage of fluids is desirable.) First, referring to FIG. 2(a), distal end D of endoscope E may be inserted transorally into the stomach of a patient, and an intense light source L disposed within endoscope E may be used to transilluminate the stomach wall S and the abdominal wall A of the patient so as to indicate externally a desired incision site. While the aforementioned transillumination process is conducted, a supply of gas may be used to inflate the patient's stomach, thereby distending the stomach and facilitating the transillumination process.

Figure 1A:
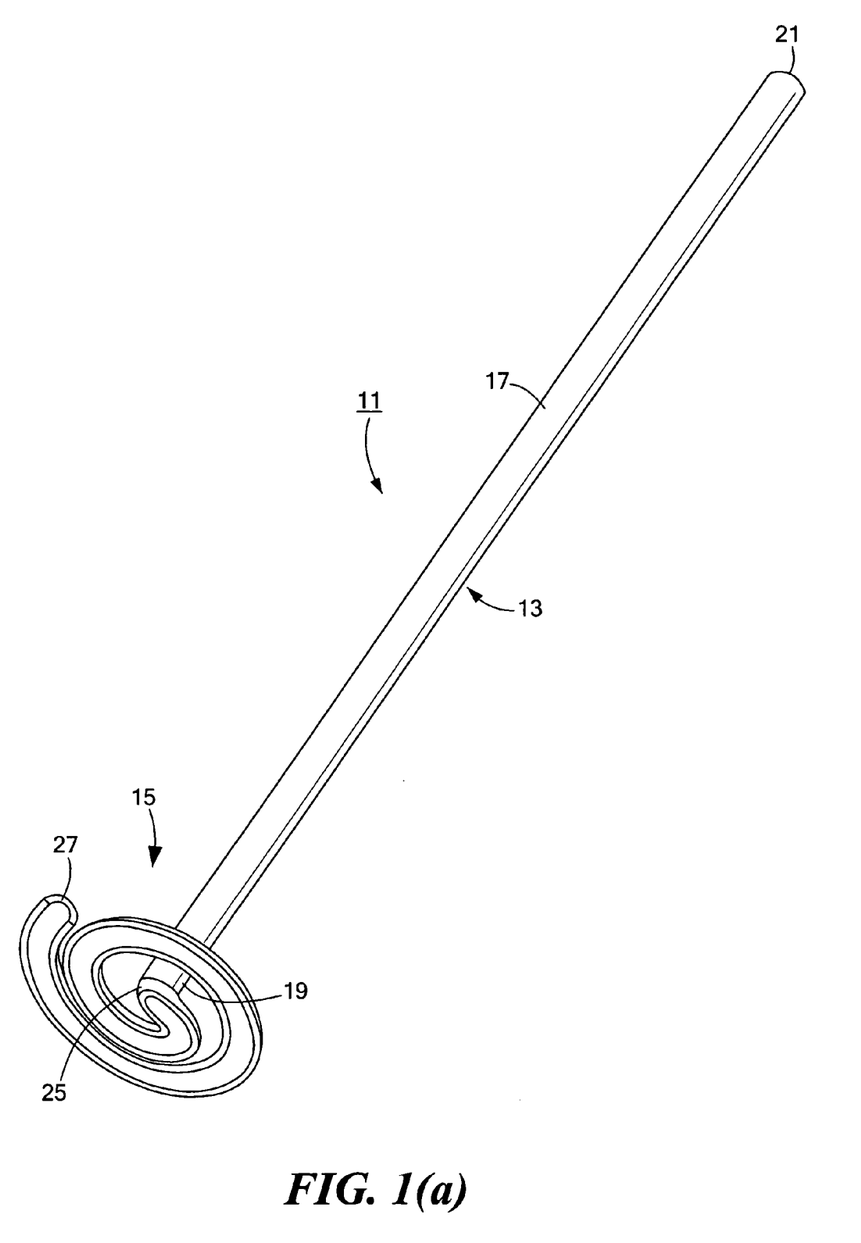
FIGS. 1(a) through 1(e) are perspective, side, top, bottom, and longitudinal section views, respectively, of a first embodiment of a catheter assembly constructed according to the teachings of the present invention, the internal bolster of the catheter assembly being shown in its coiled state.
Figure 1B:
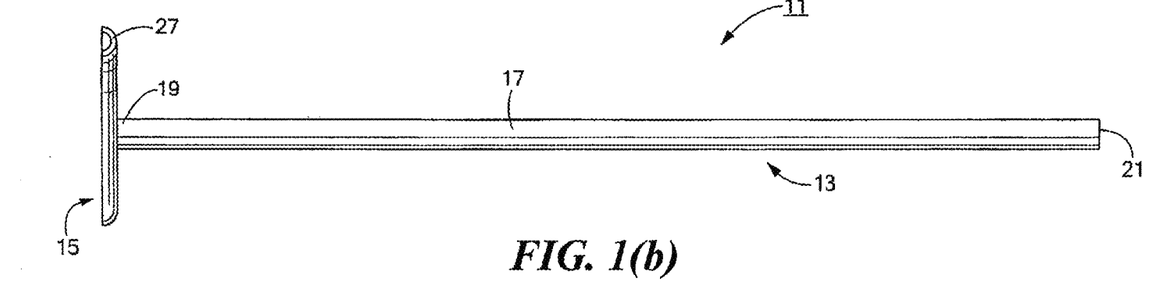
Figure 1C:
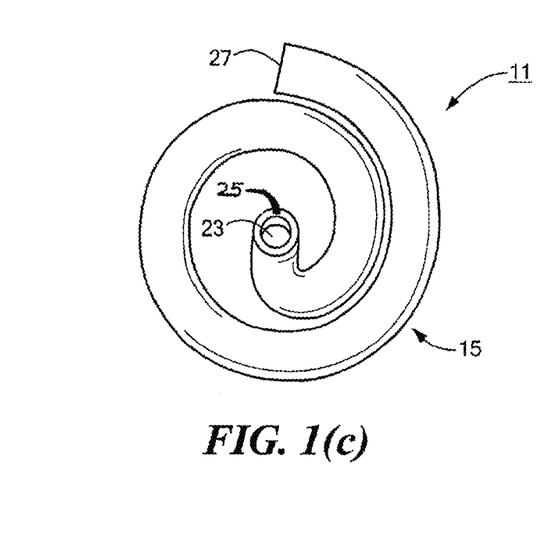
Figure 1D:
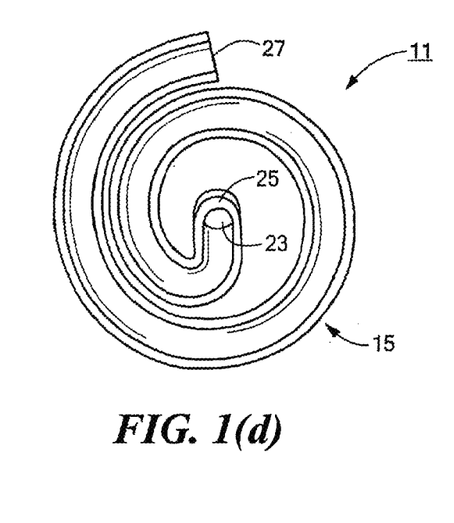
Figure 1E:
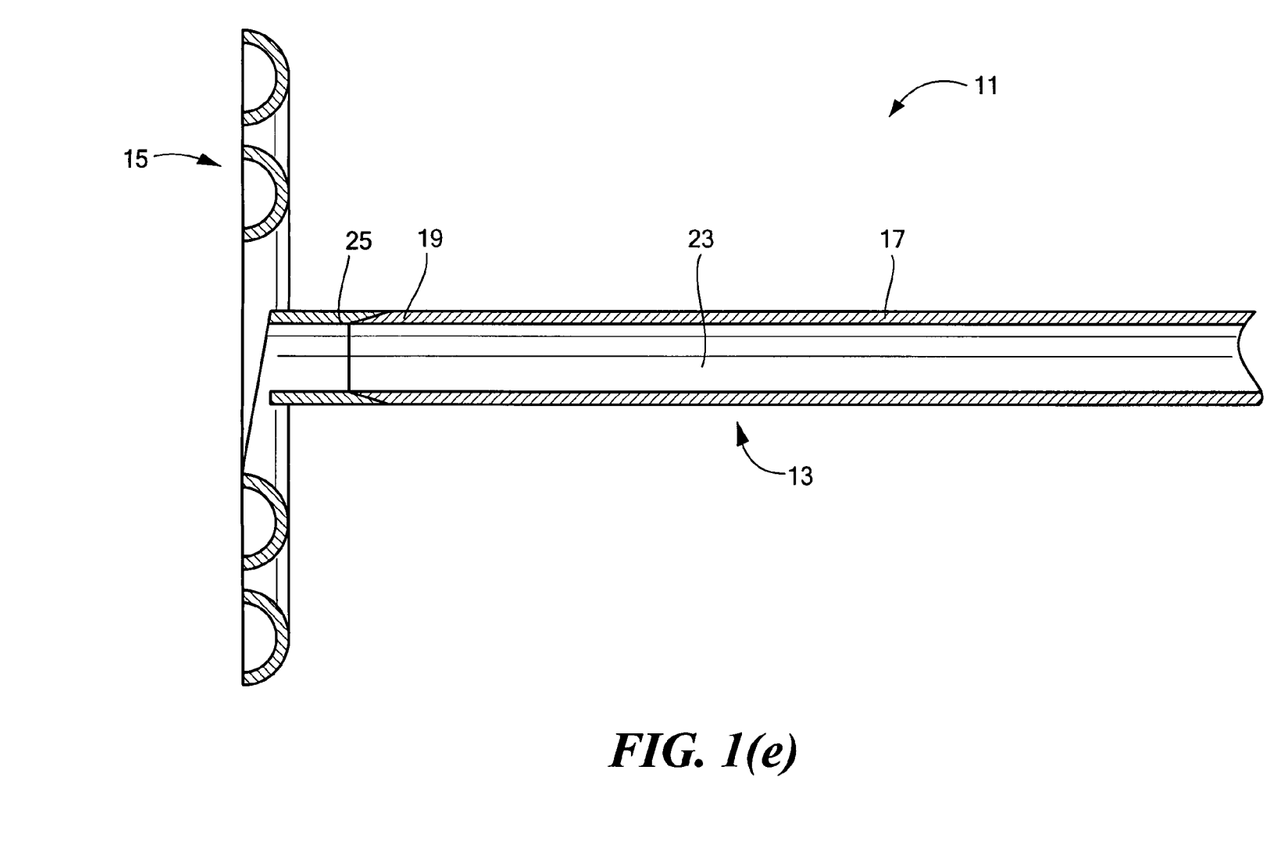
Figure 2A:
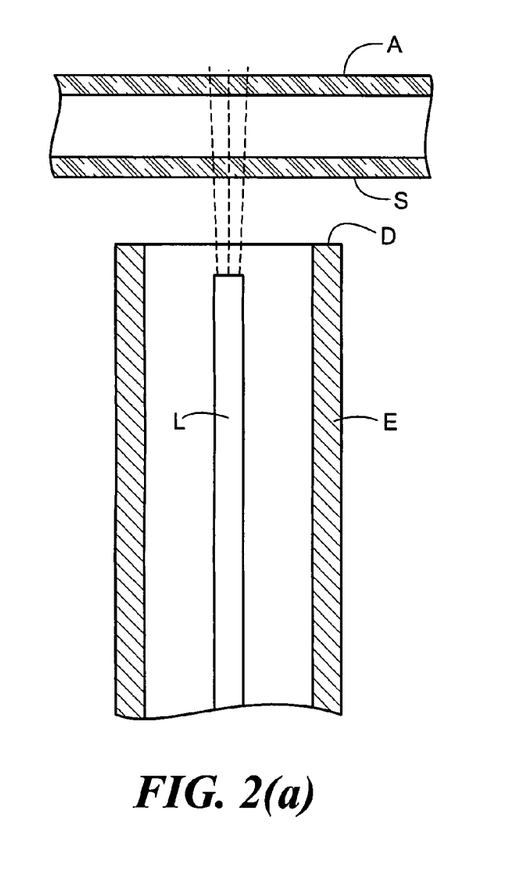
FIG. 2(a) through 2(e) are fragmentary schematic views, partly in section, illustrating a first manner in which the catheter assembly of FIGS. 1(a) through 1(e) may be implanted in a patient in accordance with the teachings of the present invention.
Figure 2B:
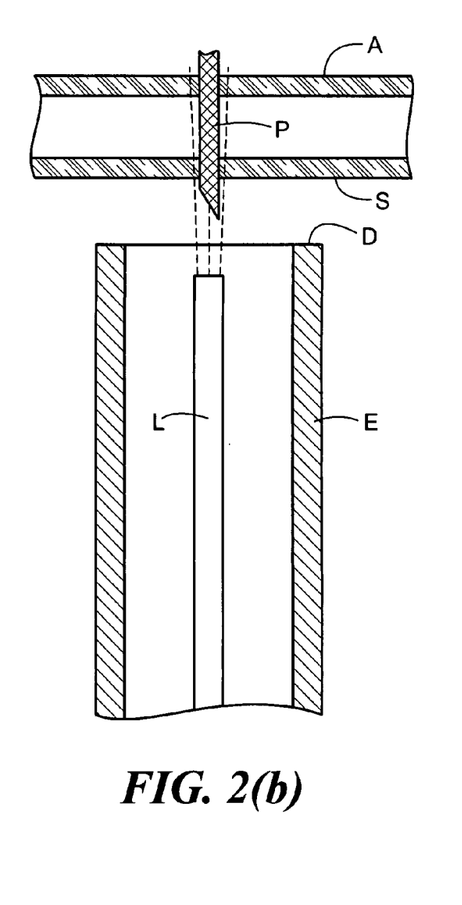
Figure 2C:
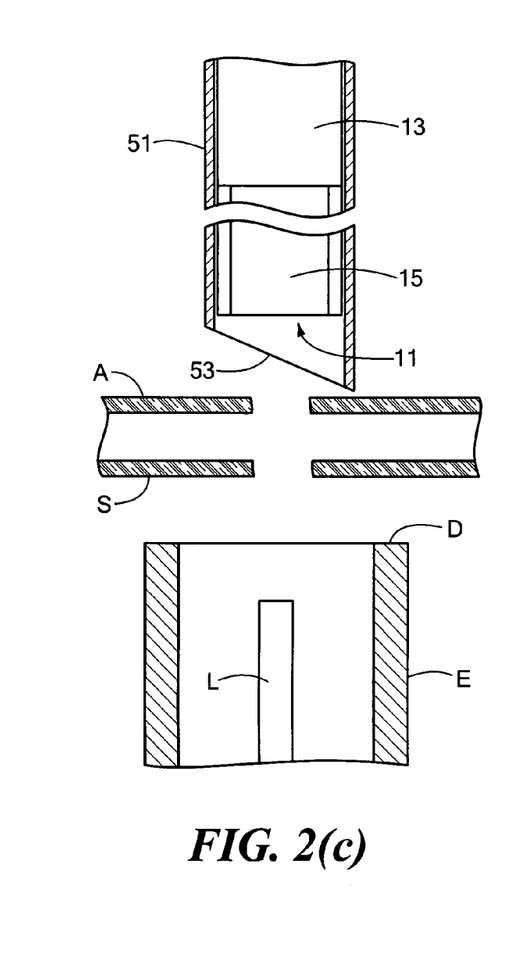
Figure 2D:
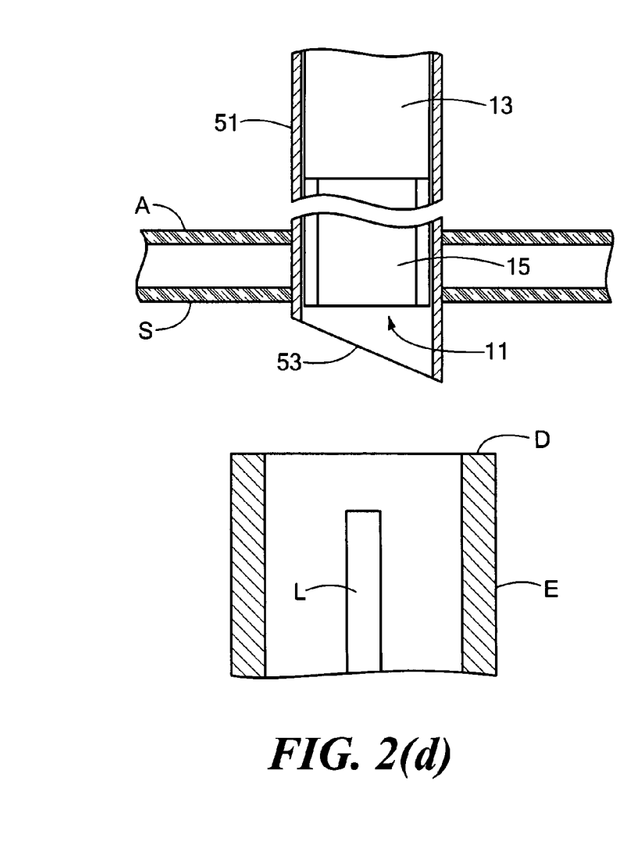
Figure 2E:
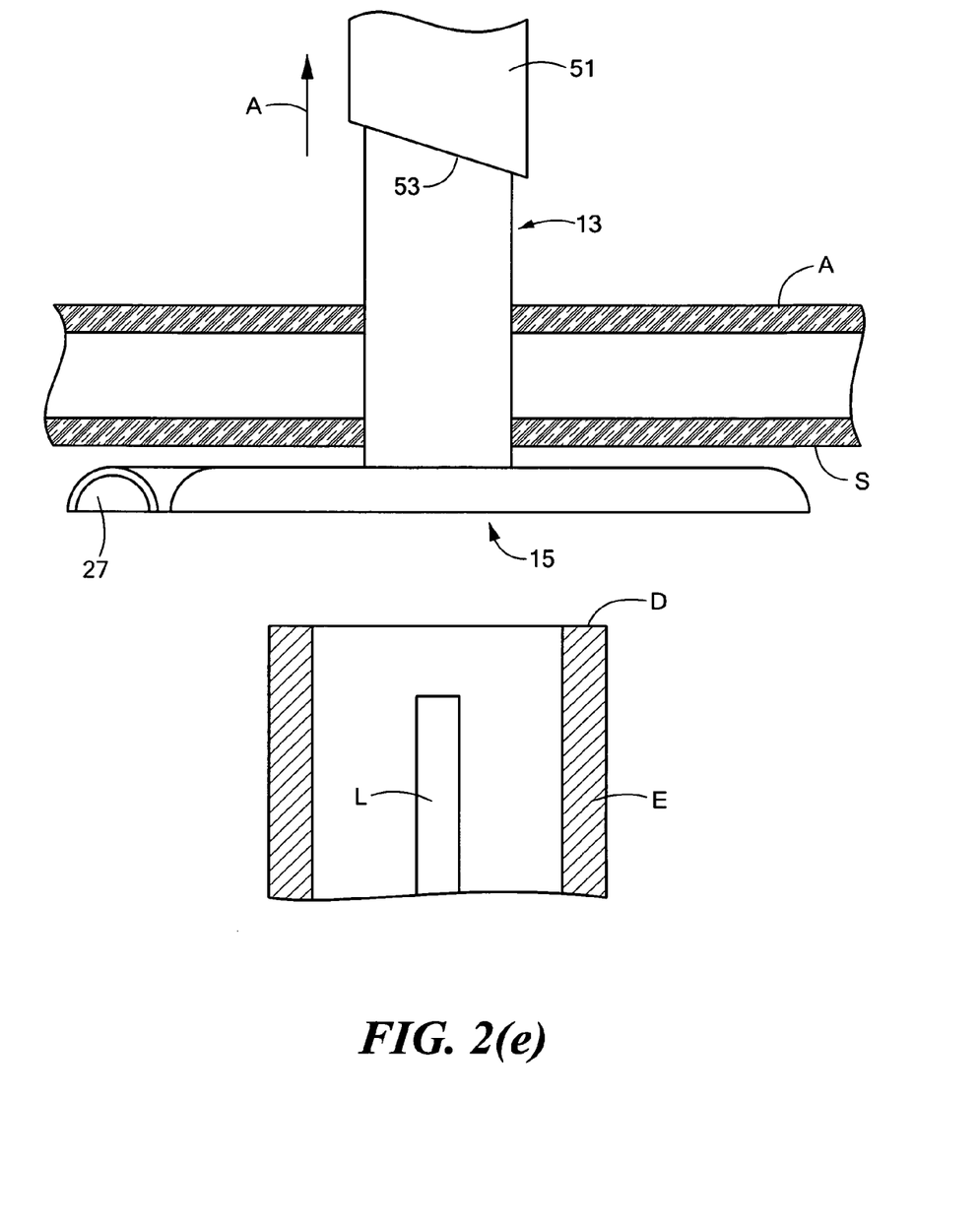

Next, as seen in FIG. 2(b), using a scalpel P, incisions may be made in the abdominal wall A and in the stomach wall S of the patient at the desired incision site. Next, as seen in FIG. 2(c), assembly 11 (which is not shown in section) may be loaded into a delivery device 51, delivery device 51 being a tubular member whose inner diameter is appropriately dimensioned to receive assembly 11 and to unwind bolster 15 to a straightened state. (As can be seen, when bolster 15 is straightened in this manner, the semi-tubular channel of bolster 15 becomes aligned with the longitudinal bore of catheter 13.) As shown in the present embodiment, delivery device 51 may have a sharpened distal end 53 to facilitate its insertion through abdominal wall A and stomach wall S. Next, as seen in FIG. 2(d), the distal ends of delivery device 51 and assembly 11 are inserted through abdominal wall A and stomach wall S at the incision site. It should be noted that, in addition to being used to straighten bolster 15, delivery device 51 may also provide stiffening support to catheter 13, which may possess limited inherent stiffness and, therefore, may not easily be inserted by itself through the incision site. Next, as seen in FIG. 2(e), while keeping assembly 11 stationary, delivery device 51 may be withdrawn from the patient in the direction indicated by arrow A. The removal of device 51 from bolster 15 permits bolster 15 to assume its relaxed, wound state, lying in a plane perpendicular to the longitudinal axis of catheter 13, thereby causing catheter 13 to be anchored within the stomach of the patient. The implanted device may then be endoscopically checked for proper placement, cut to a desired length, and secured to an external bolster, Y-port and/or clamp in the conventional manner. Food and/or medications may then be delivered to the patient through bore 23 of catheter 13.

When catheter assembly 11 is thus implanted in a patient, catheter assembly 11 may be able to withstand a substantial pull force applied to second end 21 of catheter 13, without permitting assembly 11 to be withdrawn from the patient.

To safely remove assembly 11 from a patient, one may insert delivery device 51 over the implanted assembly 11, thereby causing bolster 15 to be unfurled, and may then remove delivery device 51 and assembly 11 together from the patient.

Referring now to FIGS. 3(a) through 3(e), there is schematically shown an alternative manner in which catheter assembly 11 may be implanted in a patient. First, referring to FIG. 3(a), distal end D of endoscope E may be inserted transorally into the stomach of a patient, and an intense light source L disposed within endoscope E may be used to transilluminate the stomach wall S and the abdominal wall A of the patient so as to indicate externally a desired incision site. Preferably, while the aforementioned transillumination process is conducted, a supply of gas may be used to inflate the patient's stomach, thereby distending the stomach and facilitating the transillumination process.

Figure 3A:
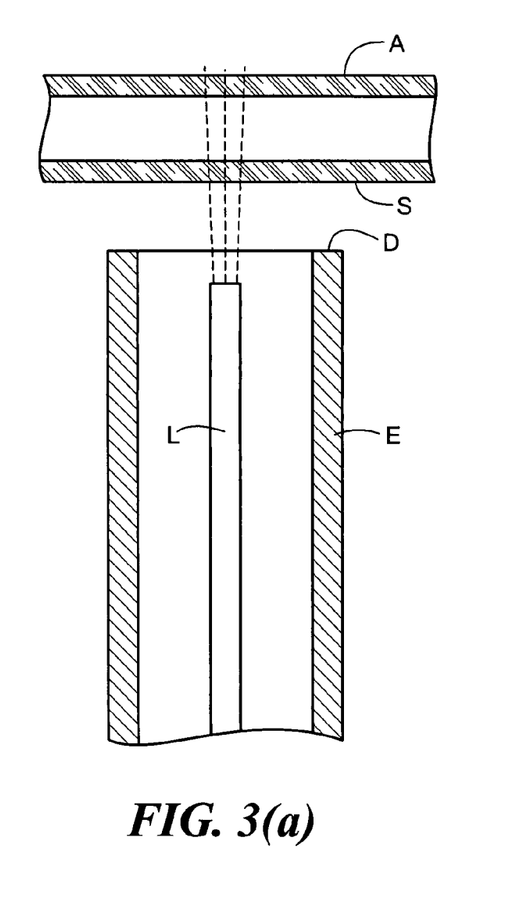
FIGS. 3(a) through 3(e) are fragmentary schematic views, partly in section, illustrating an alternative manner in which the catheter assembly of FIGS. 1(a) through 1(e) may be implanted in a patient in accordance with the teachings of the present invention.
Figure 3B:
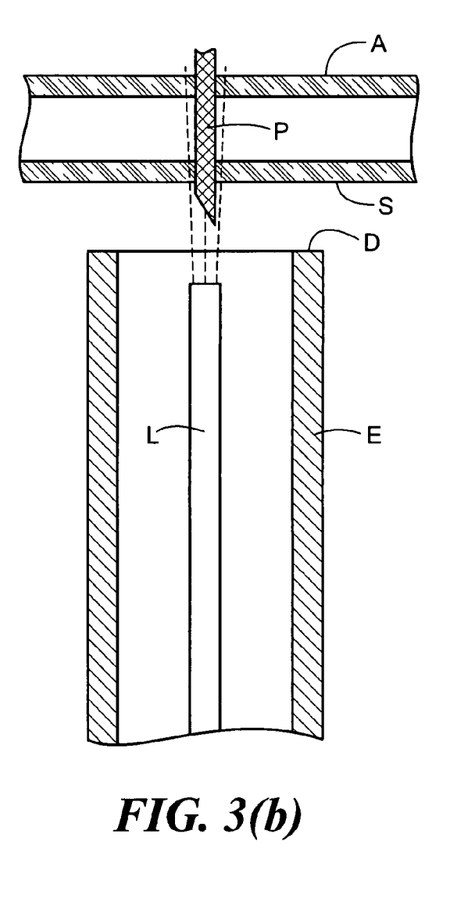
Figure 3C:
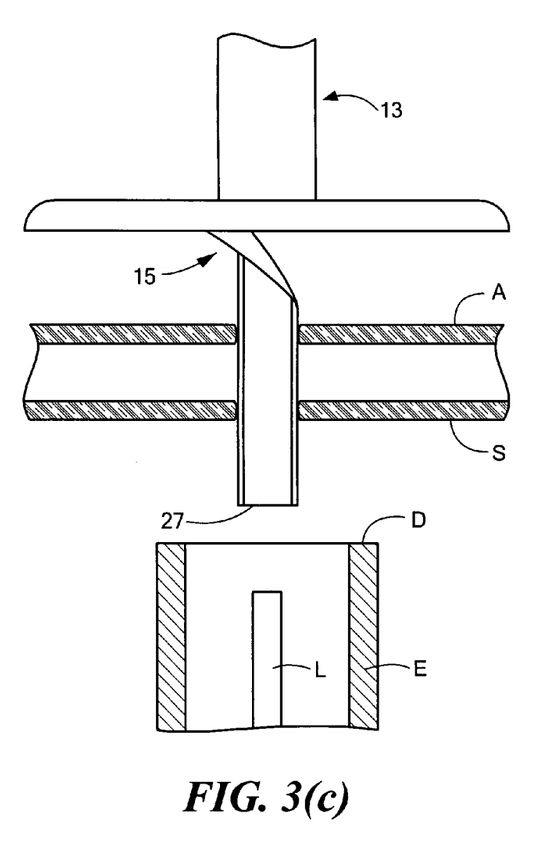
Figure 3D:
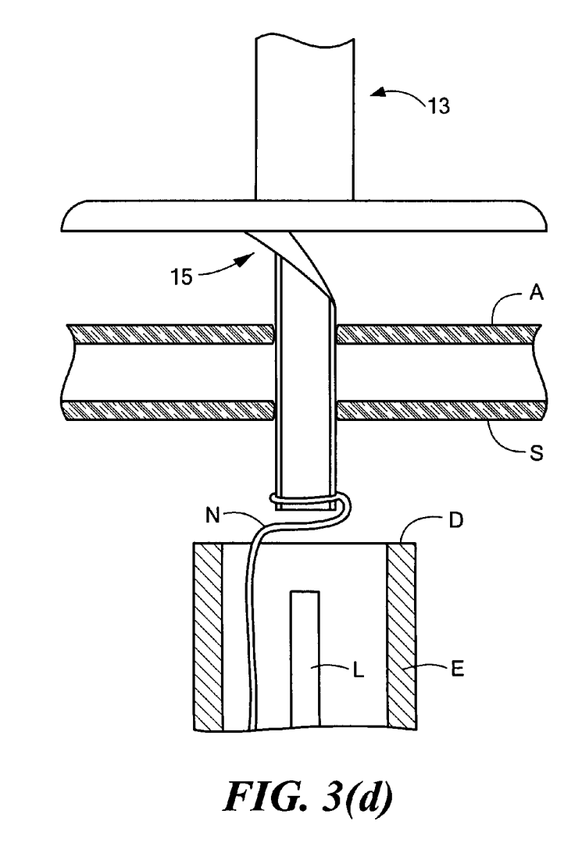
Figure 3E:
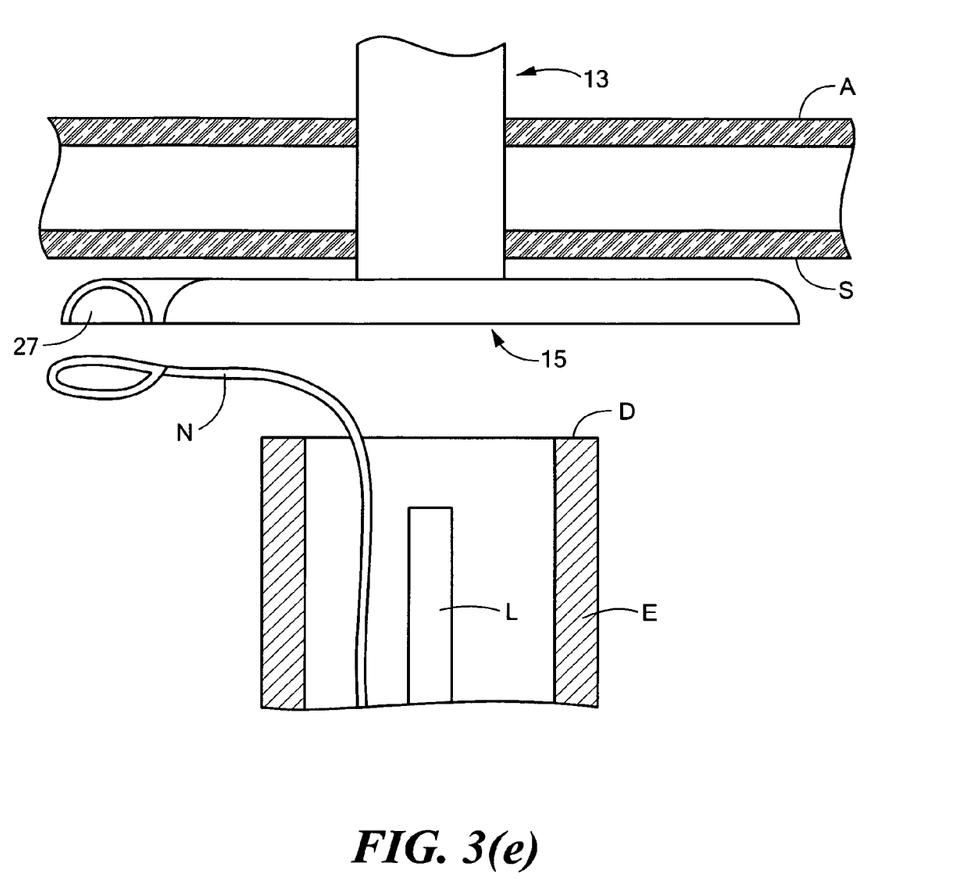

Next, as seen in FIG. 3(b), using a scalpel P, incisions may be made in the abdominal wall A and in the stomach wall S of the patient at the desired incision site. Next, as seen in FIG. 3(c), bolster 15 (assembly 11 not being shown in section) may be partially unwound from outer end 27, and the thus unwound outer end 27 may be inserted through the incision made in abdominal wall A and stomach wall S. Both the unwinding of bolster 15 and the insertion of outer end 27 of bolster 15 through the abdominal and stomach walls may be performed manually. Next, as seen in FIG. 3(d), outer end 27, which is now located in the stomach, may be grasped by an endoscopic snare N (or other grasping device), snare N then pulling the remainder of bolster 15 through the incisions in abdominal wall A and stomach wall S. Next, as seen in FIG. 3(e), with the entirety of bolster 15 having been pulled through the incisions in abdominal wall A and stomach wall S, snare N releases outer end 27, thereby causing bolster 15 to return to its coiled state. The implanted device may then be endoscopically checked for proper placement, cut to a desired length, and secured to an external bolster, Y-port and/or clamp in the conventional manner. Food and/or medications may then be delivered to the patient through bore 23 of catheter 13.

One possible advantage of the alternative technique of FIGS. 3(a) through 3(e), as compared to the first technique of FIGS. 2(a) through 2(e), is that said alternative technique does not require the use of device 51, which, as can be appreciated, must be sufficiently long to accommodate the entirety of bolster 15 in an unwound state.

The present invention provides a number of significant advantages over conventional catheter assemblies and methods for implanting the same in a patient's body. For example, with respect to conventional PEG devices of the type that are implanted using the above-described "push" and "pull" percutaneous endoscopic techniques, one advantage of the present invention is that the feeding tube does not have to be passed through the oral cavity of the patient prior to being implanted in the stomach, but rather, is inserted directly into the stomach through the abdomen. This is advantageous because the passage of the feeding tube through the oral cavity may increase the risk of infection to the incision site as bacteria present in the oral cavity may be picked up by the feeding tube and carried to the incision site.

Moreover, the push and pull methods described above require that an endoscope be introduced into the patient twice—first to deliver the snared guidewire or suture through the patient's mouth to the clinician and then again to permit a visual inspection of the placement of the internal bolster in the patient's stomach after the PEG device has been implanted. The second intubation of the endoscope may be difficult and/or painful if damage is caused during the first placement or due to the patient's anatomy or disease state. This problem may be avoided in the present technique as the endoscope need only be inserted once into the patient. Moreover, when implanting the device according to the first technique described above, the endoscope need not include a snare; consequently, an endoscope of smaller outer diameter may be used, which may result in less trauma to the patient.

Figure 4:
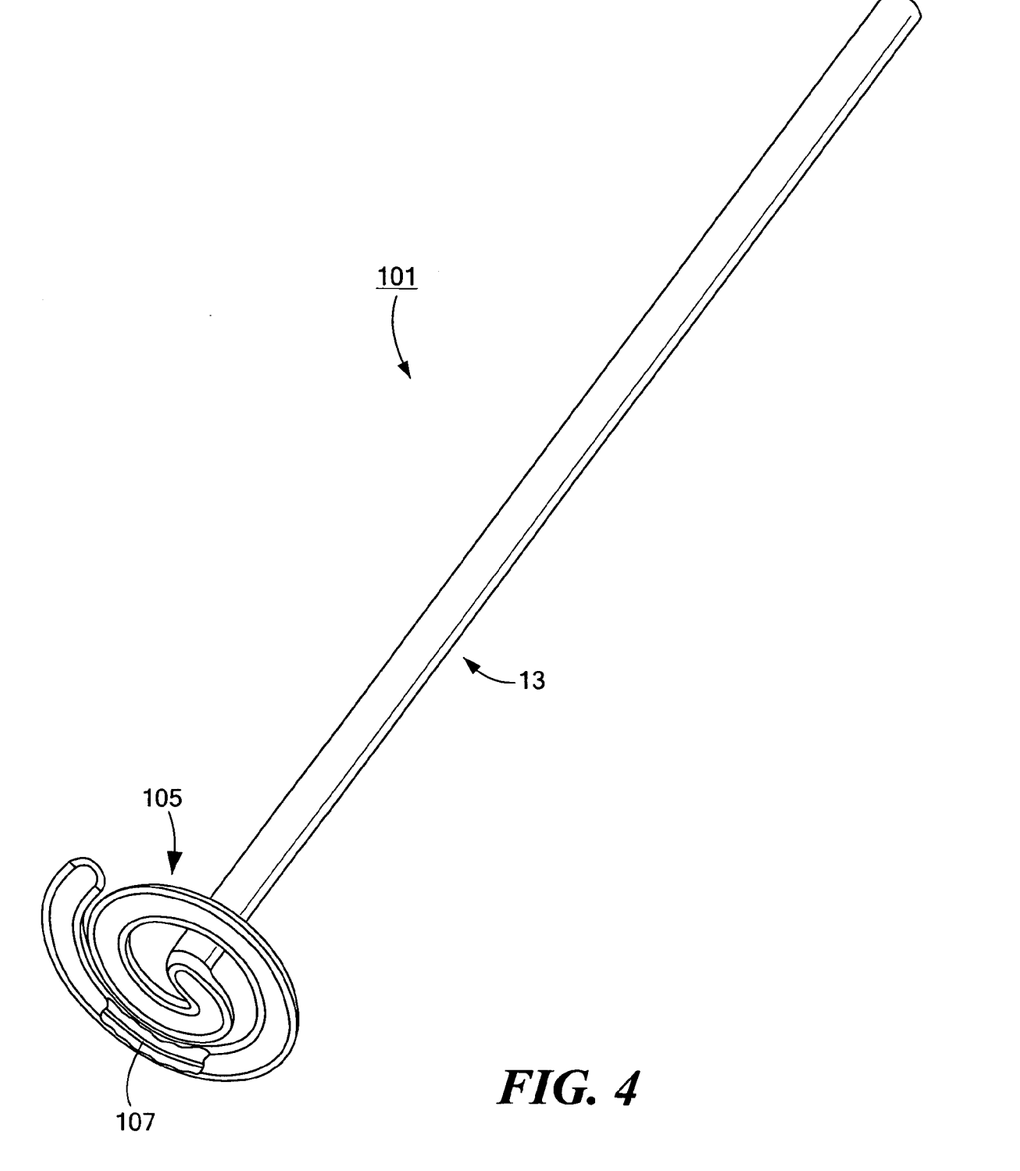
FIG. 4 is a perspective view, broken away in part, of a second embodiment of a catheter assembly constructed according to the teachings of the present invention, the internal bolster of the catheter assembly being shown in its coiled state.

Referring now to FIG. 4, there is shown a perspective view, broken away in part, of a second embodiment of a catheter assembly 101.

Assembly 101 is similar in most respects to assembly 11, one difference between the two assemblies being that assembly 101 includes a bolster 105, instead of bolster 15. Bolster 105 may differ from bolster 15 in that bolster 105 additionally may include a resilient wire 107. Wire 107, which may be made of nitinol (a nickel/titanium alloy), a shape-memory polymer, or a similar material having shape-memory properties, is embedded in the silicone rubber or other similarly flexible, biocompatible material of bolster 105 to provide structural reinforcement to bolster 105. Structural reinforcement may also be provided in the form of ribs or other related patterns. Also, there could be a second, stiffer material, either alone or embedded/coextruded with a softer material.

Assembly 101 may be implanted, used and removed in the same fashion as described above for assembly 11.

Figure 5:
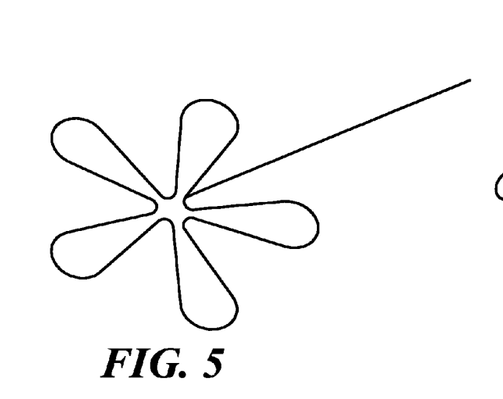
FIG. 5 is a simplified perspective view of a third embodiment of a catheter assembly constructed according to the teachings of the present invention.
Figure 6:
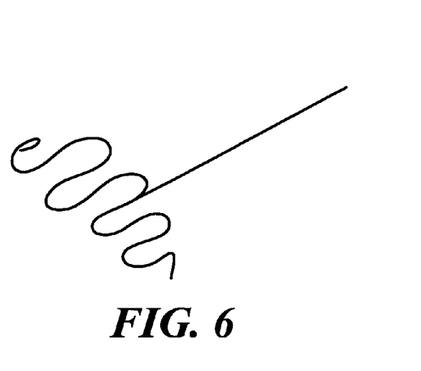
FIG. 6 is a simplified perspective view of a fourth embodiment of a catheter assembly constructed according to the teachings of the present invention.
Figure 7:
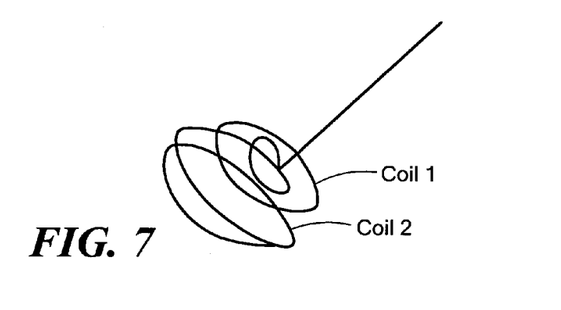
FIG. 7 is a simplified perspective view of a fifth embodiment of a catheter assembly constructed according to the teachings of the present invention.
Figure 8:
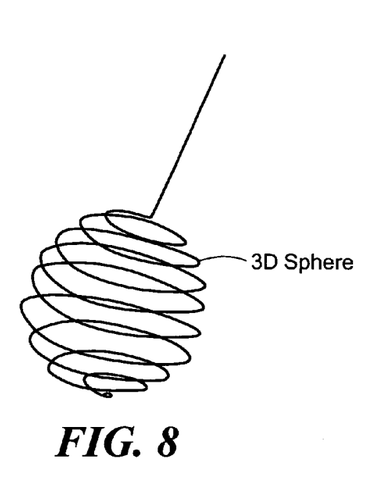
FIG. 8 is a simplified perspective view of a sixth embodiment of a catheter assembly constructed according to the teachings of the present invention.
Figure 9:
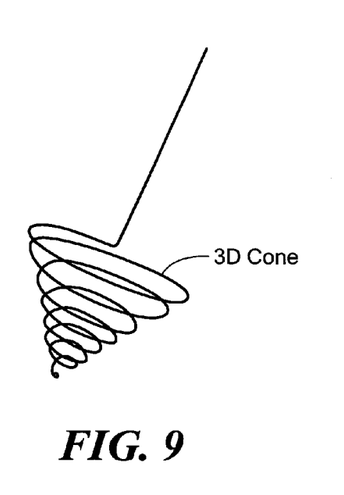
FIG. 9 is a simplified perspective view of a seventh embodiment of a catheter assembly constructed according to the teachings of the present invention.

It should be noted that, although bolsters 15 and 105 have been described herein as having a coiled shape, the bolster of the present invention is not limited to having a coiled shape. Instead, the bolster of the present invention may take the form of, for example, the petals of a flower (FIG. 5), overlapping portions, "s" curves (FIG. 6), layered shapes (FIG. 7), and three-dimensional shapes (FIGS. 8 and 9).

Also, in another embodiment (not shown), a suture may be used to retain the above-described bolsters in a wound state, one end of said suture being coupled to the outer end of the bolster, the other end of said suture being drawn through the patient, drawn taut, and coupled to a fixed member, such as an external bolster.

Additionally, it should be noted that the bolster of the present invention does not have to be a semi-tubular structure; instead, the bolster may be, for example, a full, round tube or a squashed tube.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A catheter assembly comprising:
    (a) a catheter, the catheter having a distal end and a proximal end;
    (b) an internal bolster having a proximal end, a distal end, and a semi-tubular wall forming an open side, the proximal end of the internal bolster being disposed at directly connected to the distal end of the catheter,
    the internal bolster being resiliently and reversibly transformable between a first state and a second state,
    wherein in the first state the internal bolster has a generally planar coiled shape, wherein the planar shape is generally perpendicular to the catheter, and the open side of the semi-tubular wall faces away from the catheter, and
    wherein in the second state the internal bolster is generally uncoiled and straight; and
    (c) an external bolster that engages the abdomen to prevent longitudinal movement of the catheter.

2. The catheter assembly as claimed in claim 1 wherein each of the catheter and the internal bolster comprises a silicone rubber.

3. The catheter assembly as claimed in claim 2 wherein the silicone rubber of the internal bolster has a higher durometer than the silicone rubber of the catheter.

4. The catheter assembly as claimed in claim 3 wherein the internal bolster further comprises a resilient wire embedded in the silicone rubber.

5. The catheter assembly as claimed in claim 4 wherein the resilient wire is made of a shape memory material.

6. The catheter assembly as claimed in claim 5 wherein the shape memory material comprises a metal.

7. The catheter assembly as claimed in claim 2 wherein the internal bolster further comprises a resilient wire embedded in the silicone rubber.

8. The catheter assembly as claimed in claim 5 wherein the shape memory material comprises a polymer.

9. The catheter assembly as claimed in claim 1 wherein the internal bolster includes one or more reinforcement ribs.

10. The catheter assembly as claimed in claim 1 wherein the internal bolster is insert-molded around the distal end of the catheter.

11. The catheter assembly as claimed in claim 1 wherein the catheter is a feeding tube.

12. The catheter assembly as claimed in claim 1 wherein the catheter is a gastrostomy feeding tube.

13. The catheter assembly as claimed in claim 1 wherein the internal bolster extends beyond the distal end of the catheter.

14. The catheter assembly as claimed in claim 1 wherein the distal end of the internal bolster extends beyond the distal end of the catheter in the second state.

15. The catheter assembly as claimed in claim 1 wherein the distal end of the catheter does not extend distally beyond the internal bolster.

16. The catheter assembly as claimed in claim 1 wherein the distal end of the internal bolster is open.

17. The catheter assembly as claimed in claim 1 wherein the internal bolster has a solid wall.

18. The catheter assembly as claimed in claim 1 wherein the open side faces distally.

19. The catheter assembly as claimed in claim 1 wherein the semi-tubular wall forms a semi-circle.

20. The catheter assembly as claimed in claim 1 wherein the open side is half the circumference of the tube.

21. A kit for use in implanting a catheter assembly in a patient, the kit comprising:
    (a) the catheter assembly of claim 1; and
    (b) a delivery device, the delivery device being a tubular member appropriately dimensioned to be inserted over the catheter assembly from the proximal end of the catheter and to uncoil the internal bolster.

* * * * *